United States Patent [19]

Shibata et al.

[11] Patent Number: 5,698,931
[45] Date of Patent: Dec. 16, 1997

[54] SENSOR ELEMENT AND PARTICLE SENSOR

[75] Inventors: Kazuyoshi Shibata, Nagoya; Yukihisa Takeuchi, Nishikamo-gun, both of Japan; Eric J. Shrader, Belmont, Calif.; Joseph S. Eckerle, Redmond City, Calif.; Ronald E. Pelrine, Menlo Park, Calif.

[73] Assignee: NGK Insulators, Ltd., Japan

[21] Appl. No.: 443,464

[22] Filed: May 18, 1995

Related U.S. Application Data

[63] Continuation of Ser. No. 221,014, Apr. 1, 1994, abandoned.

[51] Int. Cl.[6] .................................................. H01L 41/08
[52] U.S. Cl. .......................... 310/338; 310/324; 310/358; 73/54.24
[58] Field of Search ................................ 310/321, 358, 310/328, 324, 338; 73/54.24, 54.25

[56] References Cited

U.S. PATENT DOCUMENTS

| | | | |
|---|---|---|---|
| 3,653,253 | 4/1972 | Olin | 73/28 |
| 3,816,773 | 6/1974 | Baldwin et al. | 310/321 |
| 3,989,311 | 11/1976 | DeBrey | 302/65 |
| 4,114,063 | 9/1978 | Nelkin et al. | 310/334 |
| 4,193,010 | 3/1980 | Kompanek | 310/321 |
| 4,214,484 | 7/1980 | Abts | 73/632 |
| 4,294,105 | 10/1981 | Kelly | 73/28 |
| 4,531,267 | 7/1985 | Royer | 310/324 |
| 4,789,804 | 12/1988 | Karube et al. | 310/321 |
| 4,841,775 | 6/1989 | Ikeda et al. | 73/704 |
| 4,908,112 | 3/1990 | Pace | 204/299 R |
| 4,933,589 | 6/1990 | Strubbe | 310/321 |
| 5,126,615 | 6/1992 | Takeuchi et al. | 310/330 |
| 5,207,090 | 5/1993 | Downing | 73/61.75 |
| 5,210,455 | 5/1993 | Takeuchi et al. | 310/328 |
| 5,245,290 | 9/1993 | Cannon et al. | 324/457 |
| 5,281,888 | 1/1994 | Takeuchi et al. | 310/366 |
| 5,283,037 | 2/1994 | Baer et al. | 422/82.01 |
| 5,363,691 | 11/1994 | Gallagher | 73/324 |
| 5,406,163 | 4/1995 | Carson et al. | 310/334 |
| 5,430,344 | 7/1995 | Takeuchi et al. | |

FOREIGN PATENT DOCUMENTS

| | | | |
|---|---|---|---|
| 0408306 | 1/1991 | European Pat. Off. | 310/358 |
| 0455342 | 11/1991 | European Pat. Off. | H01L 41/09 |
| 0526048 | 2/1993 | European Pat. Off. | H01L 41/09 |
| 59-86916 | 5/1984 | Japan | H03H 9/17 |
| 60-72277 | 4/1985 | Japan | H01L 29/84 |
| 4-132921 | 5/1992 | Japan | G01L 9/12 |
| 2115222 | 9/1983 | United Kingdom | 310/338 |
| 2249176 | 4/1992 | United Kingdom | G01N 15/02 |
| WO 93/09405 | 5/1993 | WIPO | G01F 1/30 |

OTHER PUBLICATIONS

"Electrostrictive Materials for Ultrasonic Probes in the $Pb(Mg_{1/3}Nb_{2/3})O_3$–$PbTiO_3$ System", Hiroshi Masuzawa et al., May 10, 1989, pp. 101–104, Proceedings of the 7th Meeting on Ferroelectric Materials and Their Applications, Kyoto 1989, Japanese Journal of Applied Physics, vol. #1989, Supplement 28-2.

*Primary Examiner*—Thomas M. Dougherty
*Attorney, Agent, or Firm*—Parkhurst, Wendel & Burr, L.L.P.

[57] ABSTRACT

A sensor element for detecting solid particles in a fluid includes: a detecting unit including a piezoelectric film consisting essentially of a ceramic material, a first electrode coated onto at least a portion of the outer surface of the piezoelectric film, and a second electrode coated onto at least a portion of the inner surface of the piezoelectric film; a vibrating portion consisting essentially of a second ceramic material, the detecting unit being placed on the vibrating portion so that the second electrode is coated onto at least a portion of the vibrating portion; and a fixing portion for fixing the may vibrate portion so that the vibrating portion vibrates. At least one of the detecting unit and the vibrating portion contacts-with a solid particle in the fluid so that the piezoelectric film converts the vibration into an electric signal. A particle sensor includes the sensor element. The sensor element and the particle sensor are excellent in particle detection precision and durability at low cost.

7 Claims, 4 Drawing Sheets

SENSOR ELEMENT AND PARTICLE SENSOR

This application is a continuing application of U.S. Ser. No. 08/221,014, filed Apr. 1, 1994 now abandoned.

BACKGROUND OF THE INVENTION AND RELATED ART STATEMENT

The present invention relates to a sensor element and a particle sensor having the sensor element. The sensor element includes a piezoelectric film for detecting particles in a fluid.

When fluid, which is liquid or gas, contains solid particles, it is sometimes necessary to detect the presence of the particles. Particularly, when the particles are undesirably present in fluid impeding the function of the fluid, it becomes important to detect the particles.

For instance, an internal combustion engine such as an engine for a car or an engine for a heavy machine uses gasoline or diesel fuel as its power source. These internal combustion engines employ a lubricant to reduce friction drag and abrasion on a rotating surface or a sliding surface of the engine or the like. In an internal combustion engine, particles such as a metal powder generated by abrasion may mix with the lubricant so as to accelerate the abrasion of the rotating surface or the sliding surface. Particles in the lubricant are generally removed by a filter such as an oil filter. The conditions of a lubricant can be monitored in more detail by detecting particles in the lubricant.

Use of our invention is not limited to an internal combustion engine. A lubricant is used as a mechanism for transmitting power, in devices such as a hydraulic transmission, hydraulic actuators, hydraulic servo systems, etc. It is important to control the condition of lubrication fluids, which includes controlling particles in the fluid and/or viscosity or the like of the fluid.

The presence and the density of floating particles is also important for monitoring the extent of the air pollution. For example, it is important to detect a floating particle in smoke exhausted from a factory. Note that the fluid may be a gas or a liquid and these mediums need not be moving.

One of the conventional methods used to detect particles in a fluid is that a pair of electrodes are arranged leaving a certain gap, and electric resistance between the electrodes is monitored in this method, a metal particle is detected because the electric resistance between the electrodes decreases when metal particles come in contact with both of the electrodes. However, this method cannot detect particles smaller than the gap between the electrodes nor electrically insulating particles.

In another method, a magnetic field is generated in a detecting unit by an electric magnet or the like so as to detect the amount of particles accumulated. However, this method cannot detect particles not having ferromagnetism, therefore its usefulness is limited.

In still another method, the amount of particles in the fluid is correlated with the transmittance of a light. However, the transmittance of the fluid is not always constant, and dirt on a window for incident light or a window for detected light has a serious influence on accuracy, which limits durability of the sensor.

SUMMARY OF THE INVENTION

The present invention solves the problems described above and provides a sensor element and a particle sensor having excellent detection accuracy and durability at a low cost.

One aspect of the present invention provides a sensor element for detecting a foreign solid particles in a fluid, the sensor element including a vibrating portion having a sufficiently small mass for responding to a collision with a solid particle and an apparatus for converting a vibration of the vibrating portion into an electric signal so as to detect the vibration.

According to the present invention, the apparatus preferably has at least one means for the conversion from the group consisting of piezoelectric means, electromagnetic-induction means, electrical capacitance means, means for emitting light into said vibrating portion and for detecting a change in the light at a portion for receiving the light, and means for converting a change in an electric resistance due to a strain in a semiconductor into an electric signal.

Another aspect of the present invention provides a sensor comprising: a detecting unit including a piezoelectric film consisting essentially of a first ceramic material, a first electrode coated onto at least a portion of the outer surface of the piezoelectric film, and a second electrode coated onto at least a portion of the inner surface of the piezoelectric film; a vibrating portion consisting essentially of a second ceramic material, the detecting unit being placed on the vibrating portion so that the second electrode is coated onto at least a portion of the vibrating portion; and a fixing portion for holding the vibrating in specific vibrational modes portion so that the vibrating portion may vibrate; wherein when a solid particle in the fluid strikes the detecting unit and/or the vibrating portion, the vibrating portion vibrates, and said piezoelectric film converts the vibration into an electric signal.

The vibrating portion and the fixing portion may be portions of a ceramic substrate having a unitary structure, and said ceramic substrate is preferably formed with a cavity so that said vibrating portion has a plate shape having a relatively small thickness.

The first ceramic material preferably comprises at least one species selected from the group consisting of lead zirconate, lead magnesium niobate, lead nickel niobate, lead zinc niobate, lead manganese niobate, lead antimony stanate, lead titanate, and barium titanate. The fluid is preferably a lubricant. The piezoelectric film preferably has a thickness ranging from 1 to 100 micrometers, and the vibrating portion has a thickness ranging from 1 to 100 micrometers.

The vibrating portion preferably comprises stabilized zirconium oxide.

Still another aspect of the present invention provides a particle sensor comprising: (a) a sensor element comprising: a detecting unit including a piezoelectric film consisting essentially of a first ceramic material, a first electrode coated onto at least a portion of the outer surface of said piezoelectric film, and a second electrode coated onto at least a portion of the inner surface of said piezoelectric film; a vibrating portion consisting essentially of a second ceramic material, said detecting unit being placed on said vibrating portion so that said second electrode is coated onto at least a portion of said vibrating portion; and a fixing portion for holding said vibrating portion so that said vibrating portion may vibrate; wherein when a solid particle in the fluid strikes the a detecting unit and/or said vibrating portion, the vibrating portion vibrates, and said piezoelectric film converts the vibration into an electric signal; and (b) a protection cover covering the detecting unit.

Still another aspect of the present invention provides a method for detecting a solid particle in a fluid, wherein a sensor element is moved in relation to the fluid to be tested so that a foreign solid particle in the fluid to be tested is caused to collide with the vibrating portion.

In a sensor element of the present invention, the detecting unit or the vibrating portion vibrates when a solid particle in the fluid contacts with the vibrating portion of the detecting unit. The piezoelectric film of the detecting unit converts the vibration into an electric signal, and the electrodes between which the piezoelectric film is placed pickup the electric signal. The particle sensor detects a particle by means of the output signal on these electrodes. The sensor element of the present invention can measure a viscosity of a fluid by excitation of the piezoelectric element with an external voltage source and measuring the response characteristics.

PREFERRED EMBODIMENTS OF THE INVENTION

Figure 1:
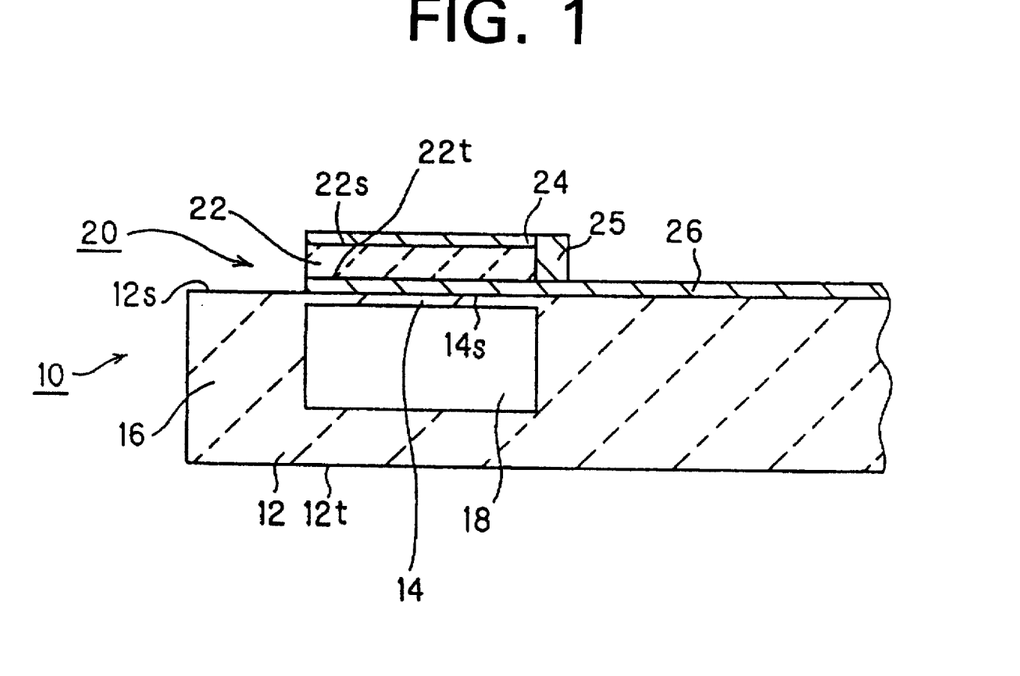
FIG. 1 is a cross-sectional view of a sensor element of the present invention, i.e., a cross-sectional view of FIG. 3 at the line A—A.
Figure 2:
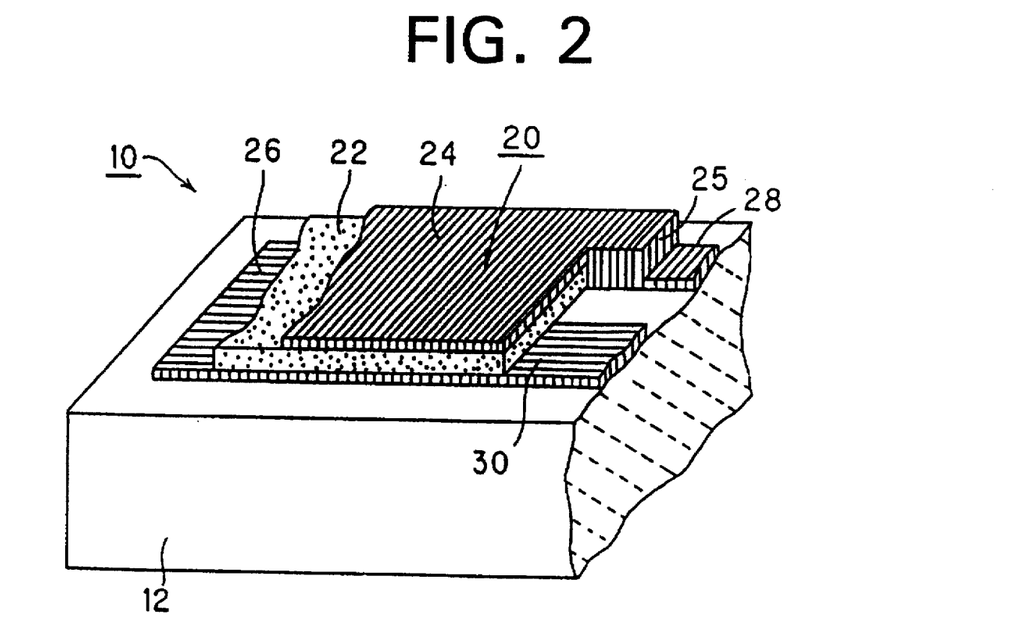
FIG. 2 is a perspective view of an example of a sensor element of the present invention.
Figure 3:
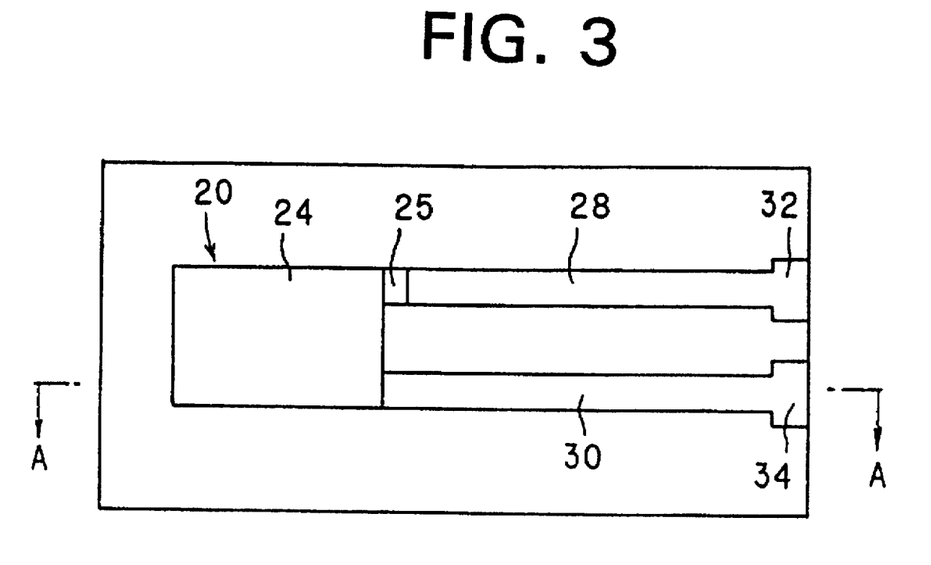
FIG. 3 is a top view of an example of a sensor element of the present invention.

FIG. 1 is a cross-sectional view of a sensor element 10 of the present invention. FIG. 2 is a perspective view of the sensor element 10 of FIG. 1, a portion of a piezoelectric film 22 and a portion of the upper electrode 24 are omitted for convenience in its explanation. FIG. 3 is a top view of the sensor element 10 of FIG. 1.

Referring to FIG. 1, the sensor element 10 has a substrate 12 and a detecting unit 20 placed on a vibrating portion 14. The substrate 12 has a monolithic structure. The vibrating portion 14 and a fixing portion 16 are portions of the substrate 12. The detecting unit 20 is placed on the upper side of the vibrating portion 14. The fixing portion 16 is positioned at the lower side of the vibrating portion 14 so as to surround the vibrating portion 14. However, it is not necessary in the present invention that the vibrating portion and the fixing portion be portions of the substrate. For example, a metal fixing portion may fix an independent vibrating portion made of ceramic. When the fixing portion is made of metal, the surface of the vibrating portion to be connected to the fixing portion may be metallized so that the metallized layer may be bonded to the fixing portion by soldering. Alternatively, the vibrating portion may be attached to the fixing portion by simply pressing it into a suitable recess. A metal such as stainless steel or iron may be employed for the fixing portion.

Figure 6A:
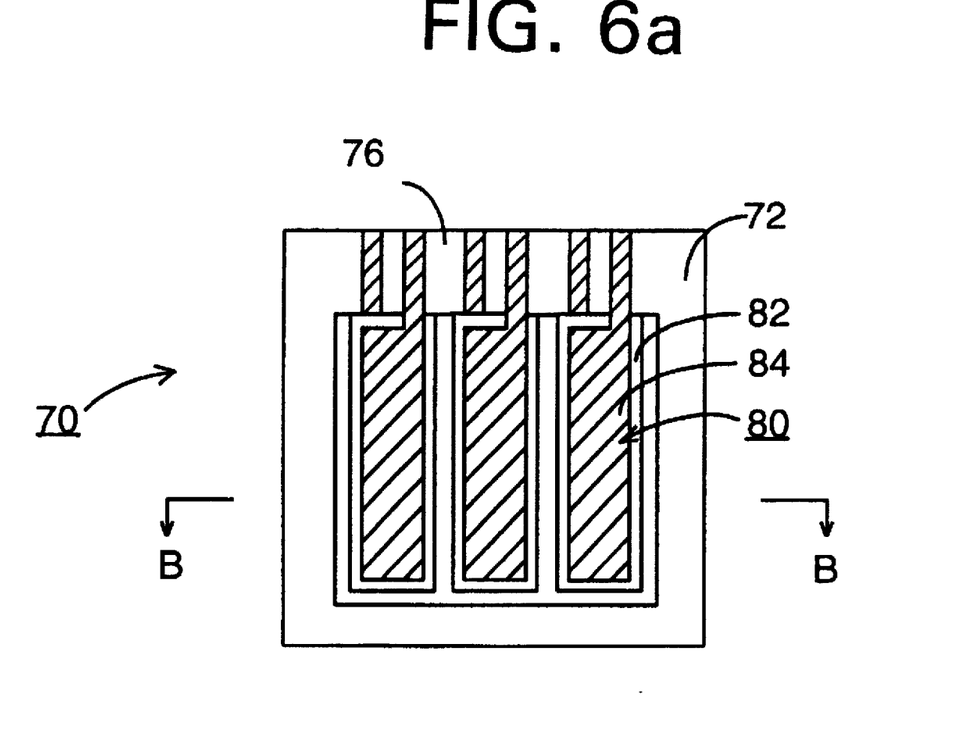
FIG. 6(a) is a top view of an example of a sensor element of the present invention.
Figure 6B:
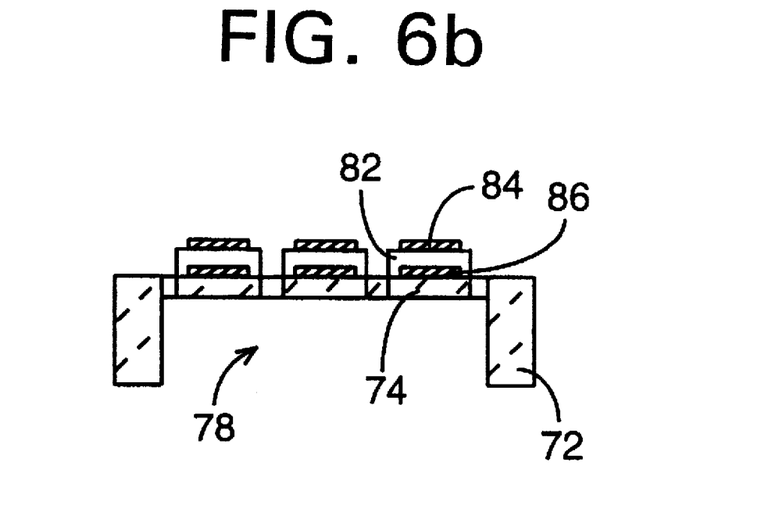
FIG. 6(b) is a cross-sectional view at the line B—B.

In the present invention, it is not necessary that the entire circumference of the vibrating portion be supported by the fixing portion as shown in FIG. 1. As illustrated in FIG. 6(a) and FIG. 6(b), only one end of the circumference of the vibrating portion 74 may be supported by the fixing portion 76 using a so-called cantilevered configuration. It is possible that at least a part of the vibrating portion or at least a part of the circumference of the vibrating portion is supported by the fixing portion.

The substrate 12 is formed with a closed cavity 18 so that said vibrating portion 14 has the shape of a thin plate or diaphragm. The detecting unit 20 is placed so as to correspond to the position of the closed cavity 18. However, the present invention is not limited to a closed cavity. For example, the cavity may be a depression approaching the vibrating portion 14 from the surface 12t of the substrate 12.

The vibrating portion 14 vibrates with the detecting unit 20 vertically, i.e., in the direction toward the detecting unit 20 or toward the cavity 18 when the sensor element 10 detects a particle. Preferably, the vibrating portion 14 has a plate shape because this shape is suitable for its vibration. In this case, the thickness of the plate is preferably 1–100 μm, more preferably, 3–50 μm, furthermore preferably, 5–20 μm.

The vibrating portion 14 is preferably made of a material able to withstand high temperatures so as to prevent thermal degeneration of the vibrating portion. The piezoelectric film 22 is placed directly on the vibrating portion 14 without any material (such an organic adhesive which cannot withstand high temperature), therebetween. The vibrating portion 14 also must not be damaged when the piezoelectric film 12 is formed. When the invention is used for a lubricant such as oil, it sometimes happens that the vibrating portion contacts with an organic solvent contained in the lubricant or that the lubricant changes to acidic or basic solution. Therefore, the vibrating portion is preferably made of a chemically stable material.

The vibrating portion 14 is preferably made of an electric insulator because the second electrode covering at least a part of the vibrating portion 14, leads connected to the first electrode and to the second electrode, lead terminals, and the like are all electrically conductive. Therefore, the vibrating portion 14 may be made of a metal having good high temperature properties, which is covered with a ceramic such as glass. Most preferably, the vibrating portion 14 is made of ceramic. For example, zirconium oxide that is stabilized, aluminum oxide, magnesium oxide, mullite, aluminum nitride, silicon nitride, glass, or the like can be suitably used for the vibrating portion. Zirconium oxide that is stabilized is preferable because it has high mechanical strength and high toughness even if the vibrating portion is thin, and low chemical reactivity with the piezoelectric film and electrodes, etc.

Zirconium oxide that is stabilized includes stabilized zirconia and partially stabilized zirconia. Zirconium oxide that is stabilized does not undergo a phase transition since it has a crystal structure such as the cubic system. On the other hand, zirconium oxide undergoes a phase change between a monoclinic structure and a tetragonal structure at around 1000° C. This phase change may generate cracks. Zirconium oxide that is stabilized contains 1–30% by mole of calcium oxide, magnesium oxide, yttrium oxide, scandium oxide, ytterbium oxide, cerium oxide, or a stabilizer such as a rare earth metal oxide. Preferably, the stabilizer contains yttrium oxide so as to enhance mechanical strength of the vibrating portion. The amount of yttrium oxide contained in the stabilizer is preferably 1.5–6% by mole, more preferably 2–4% by mole. Further, the main crystalline phase may belong to the tetragonal system or a mixture of the tetragonal system and the cubic system.

The ceramic composing the vibrating portion 14 preferably contains 0.5–5% by weight of silicon oxide, more preferably 1–3% by weight, because silicon oxide prevents an excessive reaction between the vibrating portion 14 and the detecting unit 20 upon forming the detecting unit 20 by thermal treatment.

When the vibrating portion 14 consists of ceramic, it is composed of numerous grains. The average diameter of the grains is preferably 0.05–2 μm, more preferably 0.1–1 μm.

The fixing portion 16 fixes at least a part of the vibrating portion 14 or at least a part of the circumference of the vibrating portion 14. In the mode of operation shown in FIG. 1, the fixing portion 16 preferably consists of ceramic. The ceramic material for fixing portion 16 may be the same as that of the vibrating portion, or may be different. Zirconium oxide that is stabilized, mullite, aluminum oxide, magnesium oxide, aluminum nitride, silicon nitride, glass, or the like, is suitable for the ceramic composing the fixing portion as well as for the vibrating portion 14.

The shape of closed cavity 18 is not limited. A shape of the horizontal or vertical cross section of the cavity may be, for example, a circle, an oval, a polygon including a square and a rectangle, or combinations thereof. However, when the shape is a polygon or the like, the corners are preferably rounded so as to remove the sharp edges.

The detecting unit 20 includes a piezoelectric film 22, the first electrode 24 covering at least a part of the outer surface 22s of the piezoelectric film 22, and the second electrode 26 covering at least a part of the inner surface 22t of the piezoelectric film. The second electrode 26 covers at least a part of the outer surface 14s of the vibrating portion 14.

The piezoelectric film 22 microscopically generates dielectric polarization and macroscopically outputs an electric signal, for example, electric charge or voltage, corresponding to stress. The piezoelectric film preferably experiences flexing displacement in the direction of the thickness when the vibrating portion 14 vibrates. When particles contact with the first electrode and/or the vibrating portion, the piezoelectric film 22 vibrates with the vibrating portion 14. This vibration gives rise to stresses to the piezoelectric film 22.

The piezoelectric film preferably has a thickness of 1–100 μm, more preferably 5–50 μm, furthermore preferably 5–30 μm.

A piezoelectric ceramic can be suitably used for the piezoelectric film. The piezoelectric film may be a ceramic having electrostriction or a ceramic having ferroelectricity. Further, both a material which requires a treatment for polarization and a material which does not require a treatment for polarization can serve the purpose.

The ceramic for a piezoelectric film may contain, for example, lead zirconate, lead magnesium niobate, lead nickel niobate, lead zinc niobate, lead manganese niobate, lead antimony stanate, lead titanate, barium titanate, or a combination thereof. The ceramic may contain not less than 50% by weight of a compound consisting of these as a main component. A ceramic containing lead zirconate can be preferably used. Further, oxide of lanthanum, calcium, strontium, molybdenum, tungsten, barium, niobium, zinc, nickel, manganese, or the like; a combination thereof; or other compounds may be suitably added to the above-described ceramic. For example, it is preferable to employ ceramic containing a component consisting of lead magnesium niobate, lead zirconate, and lead titanate as a main component, and further containing lanthanum and strontium.

The piezoelectric film may be dense or it may be porous. When the piezoelectric film is porous, the porosity is preferably 40% or less.

The piezoelectric film may be consist of one layer or may be a laminated film consisting of at least two layers. When the piezoelectric film is a laminated one, each of the layers may be placed horizontally or may be placed vertically.

It is also possible to place a detecting unit not only on one side of the vibrating portion but also on both sides of the vibrating portion.

In FIG. 3, the first electrode 24 and the second electrode 26 output an electric signal from the piezoelectric film 22 via a lead 28 and a lead 30 to a terminal pad 32 and a terminal pad 34. The first electrode 24 is connected to a lead 28 by a connecting portion 25. The connecting portion 25 contacts with the piezoelectric film 22 and does not contact with the second electrode 26 and the lead 30. Note, the second electrode 26, the lead 28, the lead 30, the terminal pad 32, and the terminal pad 34 may be formed simultaneously by a method for forming a thin film, which will be described later.

Each of the first electrode and the second electrode has a suitable thickness depending on its use. However, it is preferably 0.1–50 μm.

It is preferable that the first electrode be solid at room temperature and composed of electrically conductive metals. For example, metals such as aluminum, titanium, chromium, iron, cobalt, nickel, copper, zinc, niobium, molybdenum, ruthenium, rhodium, silver, tin, tantalum, tungsten, iridium, platinum, gold, lead, or the like; or an alloy thereof may be used. Needless to say, the first electrode may contain these elements in any combination. A metal belonging to the platinum group such as platinum, rhodium, palladium, or an alloy containing these metals, such as silver-platinum, or platinum-palladium is suitably used for the main component of the material for the electrode. Copper, silver, and gold are more preferable because they have durability.

The second electrode preferably consists of a simple substance containing a metal having a high melting point, such as platinum, ruthenium, rhodium, palladium, iridium, titanium, chromium, molybdenum, tantalum, tungsten, nickel, cobalt; or an alloy thereof. Needless to say, the second electrode may contain these metals having a high melting point in any combination. A metal belonging to a platinum group such as platinum, rhodium, palladium, or an alloy containing these metals, such as silver-platinum or platinum-palladium is suitably used for the main component of the material for the electrode. A metal resistant to an oxidizing atmosphere at high temperatures is preferably used for the second electrode because the second electrode is sometimes exposed to a high temperature during thermal treatment of the piezoelectric film.

A material suitably used for the second electrode may be a cermet containing a metal having a high melting point and a ceramic such as alumina, zirconium oxide, silicon oxide, or glass.

The shape of the substrate is not especially limited and is selected depending on its application. The shape of the substrate is preferably planar. However it may be cylindrical or tubular.

Figure 4:
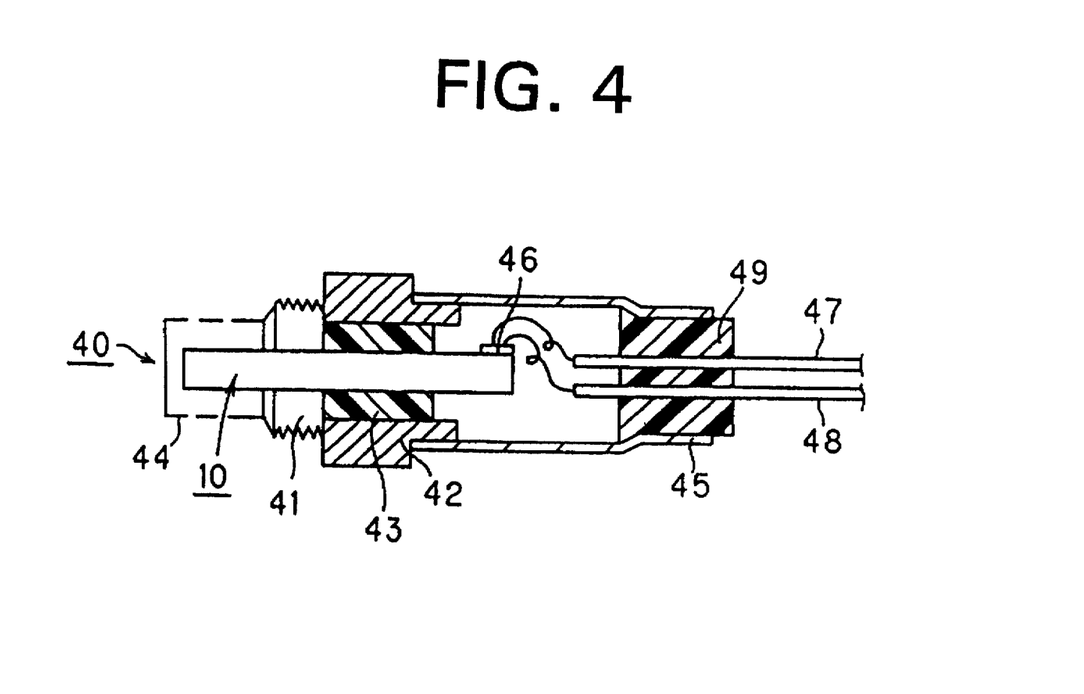
FIG. 4 is a cross-sectional view of a particle sensor of the present invention.

FIG. 4 is a cross-sectional view of a particle sensor 40 which includes the sensor element 10. The sensor element 10 can be attached to a wall (not shown) by a screw portion 41, and thereby the end portion 10a placed on the detecting unit 20 projects from the wall and contacts with a fluid to be measured.

The screw portion 41 is connected to a housing 42. Alternatively, the screw portion 41 and the housing 42 may be combined into one piece. A shock-absorbing member 43 is installed inside the housing 42 against the sensor element 10.

The end portion 10a of the sensor element 10 is covered with a protecting cover 44. The protecting cover 44 has a plurality of throughholes so that fluid can flow into the protecting cover 44.

Since the other end portion 10b of the sensor element 10 is connected to wires 46, an electric signal present on the terminal pads 32 and 34 can be transmitted to the lines 47 and 48. The end portion 10b of the sensor element 10 and the wires 46 are inserted into a casing 45. An end of the casing 45 is sealed up with an end portion member 49. The lines 47 and 48 pass through the end portion member 49.

A method for manufacturing a sensor element 10 of the present invention is hereinafter described.

Molded layers of green sheet or green tape are laminated by thermally pressing and then sintered to obtain an integrated substrate. For example, in the substrate 12 of FIG. 1, three layers of green sheets or green tapes are laminated. The second layer is formed in advance with a throughhole of a predetermined shape so as to form a closed cavity 18. The layers may be formed by press molding, slip casting, injection molding, or the like. The cavity may be formed by machining such as cutting, laser machining, blanking by press working, or the like. It is not required that the layers have the same thickness. However, it is preferable that each of the layers has the same degree of shrinkage due to sintering.

When the cavity is open (i.e., depression), green sheets or green tapes may be molded so as to have a shape corresponding to the depression before being sintered. Alternatively, the cavity may be formed by machining after sintering.

A method for forming the detecting unit 20 on the ceramic vibrating portion 14 is now described. A piezoelectric body is formed by press molding in which a mold is employed, tape forming in which slurry is employed, or the like. Before sintering, the piezoelectric body is laminated on the vibrating potion of the substrate by thermal pressing. This laminate is subjected to sintering to form a substrate and a piezoelectric body that are bonded together. This method requires that the electrode 26 be previously formed on the substrate by one of the methods for forming a film described later.

Though the sintering temperature of a piezoelectric film is suitably determined depending on the materials which compose the film, it is generally 800° C.–1400° C., preferably 1000° C.–1400° C. It is preferable that the piezoelectric film be sintered together with the presence of an evaporating source for the piezoelectric film material so as to control the composition of the piezoelectric film.

On the other hand, in a method for forming a film, the second electrode 26, the piezoelectric film 22, and the first electrode 24 are laminated on the vibrating portion 14 in this order to form the detecting unit 20. A method for forming a film in conventional art, for example, a method for forming a thick film such as screen printing, an applying method such as dipping, a method for forming a thin film such as ion beam, sputtering, vacuum deposition, ion plating, chemical vapor deposition (CVD), or plating may be used. However, a method for forming a film is not limited to these methods. The second electrode 26, the lead 28, the lead 30, the terminal pad 32, and the terminal pad 34, are simultaneously applied to the substrate by screen printing. Preferably, the piezoelectric film 22 is formed by screen printing, dipping, coating, or the like. These methods use paste or slurry which contains ceramic powders of the piezoelectric film material as a main component, and therefore the piezoelectric film 22 is formed on the substrate with the detecting unit 20 having excellent piezoelectric properties. Forming a piezoelectric film by one of these methods for forming films does not require any adhesive, and a detecting unit and a vibrating portion can be integrally connected. Therefore, such a method is particularly preferable in view of its excellent reliability, excellent reproducibility, and easy integration. The shape of such a film may be suitably patterned. A pattern may be formed by a method such as screen printing or photolithography or by removing unnecessary parts by machining such as laser machining, slicing, or ultrasonication.

The shapes for the piezoelectric film, the first electrode, and the second electrode are not limited at all and any shape may be employed. For example, they may be a polygon such as a triangle and a square, a curved shape such as a circle, an oval, and a toms, a comblike shape, a lattice, or a combination of these to form a special shape.

Each of the films 22, 24, 26, which are thus formed in a particular shape on the substrate may be subjected to thermal treatment respectively whenever each film is formed, so that the film and substrate are integrated. Alternatively, the films may be subjected to thermal treatment simultaneously so as to integrally connect the films and the substrate. When the first electrode or the second electrode is formed by a method for forming a thin film, thermal treatment is not always necessary to integrate these electrodes.

In the sensor element of the present invention, only one detecting unit is required. However, more than one detecting unit may be placed on the vibrating portion. In this case, more than one vibrating portion is preferably provided so that a vibration is independently caused corresponding to each detecting unit. When the substrate has more than one identical detecting units, the output signal can be increased for a given level of stress in the vibrating portion. On the other hand, when detecting units have different structures, various values of mechanical impedance are detected so that size, mass, and number of particles can be discriminated and detected.

Figure 5:
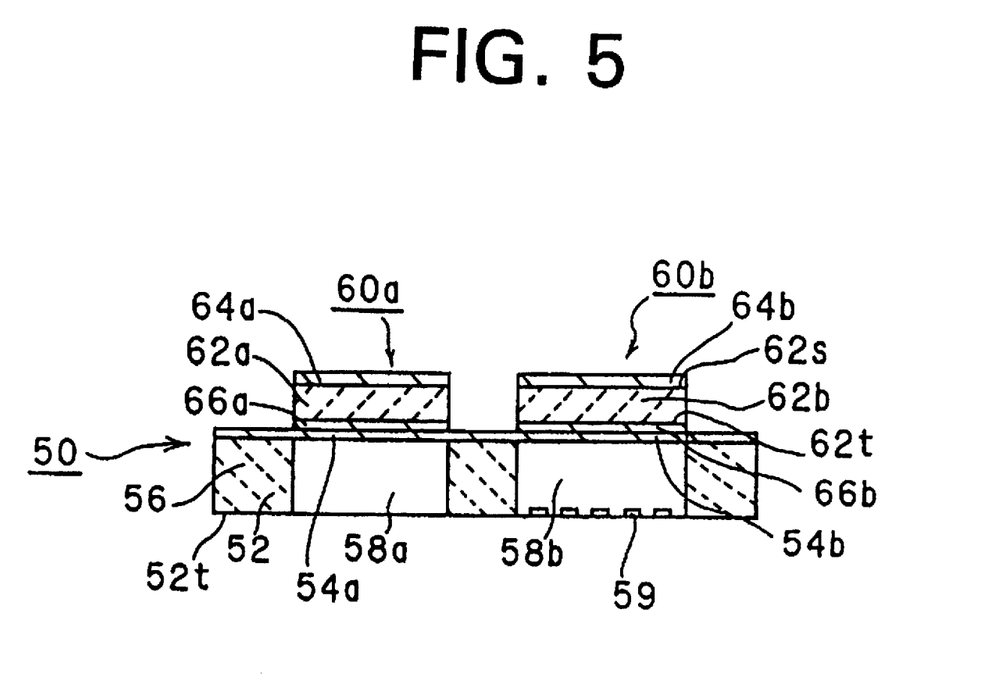
FIG. 5 is a cross-sectional view of a sensor element of the present invention.

In FIG. 5, the sensor element 50 includes the substrate 52 and the two detecting units 60a and 60b placed on the two vibrating portions 54a and 54b, respectively: In the substrate 52, the vibrating portions 54a, 54b and the fixing portions 56 are integrated. The vibrating portions 54a, 54b and the fixing portion 56 form a part of the substrate 52. The detecting units 60a and 60b are placed on the vibrating portions 54a and 54b, respectively. The depressions 58a and 58b are formed below the vibrating portions 54a and 54b, respectively, as cavities. The substrate 52 is formed with the depressions 58a and 58b facing toward the vibrating portion 54 from the surface 52t of the substrate 52 so that each of the vibrating portions 54a and 54b is relatively thin. The fixing portion 56 is positioned so as to surround the vibrating portions 54a and 54b.

The detecting units 60a and 60b have the piezoelectric films 62a and 62b, the first electrodes 64a and 64b covering at least a part of the outer surface 62s of the piezoelectric films 62a and 62b, and the second electrodes 66a and 66b coveting at least a part of the inner surface 62t of the piezoelectric films respectively. The second electrodes 66a and 66b cover at least the surface 54s of the vibrating portions 54a and 54b respectively.

It is possible to use detecting unit 60a to detect particles and to use detecting unit 60b to compensate for particles detected by detecting unit 60a. The inside of depression 58b is covered with a filter 59. Since the filter 59 is provided with fine throughholes having a predetermined size, only particles smaller than the size of the throughholes can flow into the depression 58b. When a particle in the depression 58b contacts or particularly collides with the vibrating portion 54b, the detecting unit 60b and the vibrating portion 54b vibrates, and the piezoelectric film 62b of the detecting unit 60b converts the vibration into an electric signal. Therefore, the output from the detecting unit 60b is correlated with particles having a certain size or smaller. The output from the detecting unit 50b may also indicate a baseline change such as changes in the fluid pressure and fluid speed.

On the other hand, since the depression 58a does not have any filter, particles having various sizes can go into the depression 58a. When a particle contacts with the vibrating portion 54a, the detecting unit 60a outputs an electric signal. Therefore, the output of detecting unit 60a is correlated with particles of various sizes.

Accordingly, the output of the detecting unit 60a may be compared to the output of the detecting unit 60b so as to compensate for errors in detecting particles in the fluid. Alternatively, the output of detecting unit 60a may be subtracted from the output of the detecting unit 60b so as to compensate for errors due to temperature or pressure fluctuations.

In FIG. 6(a) and FIG. 6(b), the sensor element 70 includes the substrate 72 and the three detecting units 80 placed on the three vibrating portions 74 of the substrate 72. The vibrating portions have a cantilever beam shape, and the substrate 72 has a cavity 78.

The vibrating portions 74 protrude from the fixing portion 76 which is a part of the substrate 72. The vibrating potions are flexible. The periphery of each of the vibrating portions has cuts which are connected to the cavity 74. Note that the vibrating portions are not required to be parallel to one another though the three vibrating portions 74 shown in FIG. 6(a) protrude parallel with one another.

The detecting units 80 are placed on the vibrating portions 74, respectively. The second electrodes 86 cover the surfaces of the vibrating portions 74. A part of each of the vibrating portions 74 is not covered by the second electrode, leaving a rim. The piezoelectric films 82 cover the second electrodes 86, being laminated thereon. The rims of the vibrating portions 74, which are not covered with the second electrodes 86, are covered with the piezoelectric films 82. The first electrodes 84 cover the surfaces of the piezoelectric films 82. A part of the surface of each of the piezoelectric films 82 is not covered by the first electrode 84.

The method for using the sensor element of the present invention is hereinbelow explained.

When an alternating voltage is applied to a piezoelectric film from a pair of electrodes, the detecting unit and the vibrating unit vibrate by an inverse piezoelectric effect. This effect may be used to detect particles or viscosity by applying a voltage to the electrodes. Alternatively, particles may be detected by not applying a voltage to the electrodes.

In order to detect particles in a fluid while voltage is not applied, the fluid must be flowing. Preferably the flowing speed is relatively stable. For example, when a the fluid is lubricant in a combustion engine, the operation of an oil pump or the like preferably maintains the fluid flow at a certain speed.

On the other hand, for particle detection by applying a voltage to the a pair of electrodes, an electric signal having a frequency that is tuned to be close to the resonance of the sensor element is applied to the electrodes so as to vibrate the detecting unit thereby detecting a particles in the fluid and/or detecting the fluid viscosity.

Whether or not a voltage is applied to the electrodes, the output signal from the detecting unit due to a particle is generally small, and therefore, the output signal is preferably amplified by an amplifying circuit. The output signal correlates with particle sizes and number of particles, and preferably an electric circuit including the amplifying circuit converts the output signal into a distribution of particle size so as to detect the spectrum of particle sizes in the fluid. Note that when the output signal is sufficiently large, an amplifying circuit may not be necessary.

Each impact of a particle on the vibrating portion 14 of a detecting unit will cause a voltage pulse to appear on the output terminals 32 and 34 of the device. This pulse will have a waveform generally similar to the well-know "damped sinusoid" waveform. The amplitude of the damped sinusoid waveform is proportional to the size and speed of the particle. If the speed is controlled by provision for relatively stable fluid speed as described above, then the waveform amplitude is a good measure of the size of each particle that impacts the vibrating portion. Thus, suitable electronic circuitry can be used to determine the amplitude of each damped sinusoid generated by the detecting unit. The particle size distribution is then directly determined from the distribution of damped sinusoid waveform amplitudes.

In the sensor element of the present invention; an adhesive is not required for connecting a detecting unit to vibrating unit because the detecting unit is placed directly on the vibrating portion. The sensor element can therefore be operated at a high temperature. The sensor element has high durability because an adhesive is not subject to attack by a lubricant or the like. Further, the sensor element has high sensitivity in detection because the sensor element does not use any shock-absorbing material such as an adhesive and because the piezoelectric film and the vibrating portion arc thin. Further, the sensor element can detect even a small particle and magnetic, nonmagnetic, or diamagnetic particles.

Though the present invention has been described specifically on the basis of some embodiments, the present invention should not limited to the embodiments described above. It should be understood that various alterations, modifications, and improvements, or the like can be made based on the knowledge of a person of ordinary skill without deviating from the teaching of the present invention.

What is claimed is:

1. A sensor element for detecting a solid particle in a fluid, comprising:

a substrate comprising (i) a main body having a closed-bottom recess formed in an upper surface thereof, and (ii) a thin-walled vibrating portion covering said recess so as to form a closed cavity; and a detecting unit formed on a surface of said thin-walled vibrating portion outside said closed cavity, said detecting unit comprising a piezoelectric film, a first electrode coated on at least a portion of the outer surface of said piezoelectric film, and a second electrode coated on at least a portion of the inner surface of said piezoelectric film;

wherein said detecting unit and said thin-walled vibrating portion have sufficiently low mass such that solid particles in the fluid strike said detecting unit causing said detecting unit and said thin-walled vibrating portion to vibrate, and said piezoelectric film converts the vibration into an electric signal.

2. The sensor element of claim 1, wherein said substrate is a unitary ceramic substrate, and said main body and said thin-walled vibrating portion are integral parts thereof.

3. The sensor element of claim 1, wherein said piezoelectric film comprises at least one material selected from the group consisting of lead zirconate, lead magnesium niobate, lead nickel niobate, lead zinc niobate, lead manganese niobate, lead antimony stanate, lead titanate, and barium titanate.

4. The sensor element of claim 1, wherein the fluid is a lubricant.

5. The sensor element of claim 1, wherein said piezoelectric film has a thickness ranging from 1 to 100 micrometers, and said thin-walled vibrating portion has a thickness ranging from 1 to 100 micrometers.

6. The sensor element of claim 1, wherein said thin-walled vibrating portion comprises stabilized zirconium oxide.

7. The sensor element of claim 1, further comprising a protective cover for housing at least said detecting unit of the sensor element.

* * * * *